United States Patent [19]

Stern

[11] Patent Number: 5,653,712

[45] Date of Patent: Aug. 5, 1997

[54] INTRAMEDULLARY BONE GROOVER

[76] Inventor: Howard G. Stern, 2001 Kings Lynn Rd., Midlothian, Va. 23113

[21] Appl. No.: 538,425

[22] Filed: Oct. 2, 1995

[51] Int. Cl.⁶ ................................................ A61B 17/56
[52] U.S. Cl. .......................... 606/80; 606/79; 408/153; 408/160
[58] Field of Search ............................... 606/79, 80, 81, 606/84, 85, 92, 95, 99; 407/12, 53, 64, 65; 408/160, 158, 153

[56] References Cited

U.S. PATENT DOCUMENTS

| | | | |
|---|---|---|---|
| 1,858,852 | 5/1932 | Cleveland et al. | 82/1.2 |
| 2,545,443 | 3/1951 | Bowren | 82/1.2 |
| 3,037,406 | 6/1962 | Fried | 82/1.2 |
| 3,435,729 | 4/1969 | Toth | 90/12 |
| 3,472,229 | 10/1969 | Kuntscher | 128/317 |
| 4,550,788 | 11/1985 | Park | 175/173 |
| 4,696,292 | 9/1987 | Heiple | 606/79 |
| 5,387,218 | 2/1995 | Meswania | 606/80 |

*Primary Examiner*—Michael Buiz
*Assistant Examiner*—David O. Reip

[57] ABSTRACT

Preliminary to cementing a prosthesis in a hole in an intramedullary bone, annular groves are formed in the bone around the hole by cutters radially extensible in opposite directions from a tool driven by a cannulated rotary power unit. A control rod extends through the power unit and through a cannulated shank of the tool held by the power unit. A control unit mounted on the power unit moves the control rod lengthwise to cause projection and retraction of the cutters while rotating to groove a bone as well when not rotating.

8 Claims, 4 Drawing Sheets

INTRAMEDULLARY BONE GROOVER

BACKGROUND OF THE INVENTION

1. Field of the Invention

This invention relates to chucked and motor driven intramedullary bone machining tools, specifically to such tools used in the field of orthopedic surgery.

2. Description of the Prior Art

Orthopedic Surgeons commonly use methyl-methacrylate bone cement to secure prostheses to bone. To do so, the bone is commonly machined in such a way as to allow for stable cementation of the prosthesis to bone. In hip replacement surgery, this machining process includes the use of a series of reamers to cylindrically machine the endosteal canal of the femur. This is followed by the use of a broach to further shape the endosteal canal of the femur to match the shape of the implant.

Prosthetic hip joint replacement is often performed with the use of methyl-methacrylate bone cement. Bone cement is used to secure the artificial joint component to bone. A common method used for implantation of the femoral component of a hip replacement in humans is to cement the component to the bone. To do so requires the endosteal canal of the femur to be machined to a similar shape as that of the prosthesis. A series of bone reamers and broaches is used to create a cavity in the bone of similar shape to the implant, only larger. The larger size of the bone cavity relative to the prosthesis is to allow space between the two to place bone cement. The actual size difference between the machined cavity in the bone and the prosthetic implant will determine how thick the cement will be between the prosthesis and the bone.

The strength of the cement-to-bone bond has several variables which affect that bond. These variables affect this bond's ability to withstand repetitive loading and other stresses over a long term. These variables include the purity and porosity of the cement. Also included are any contaminants present at the cement-bone interface that might affect bonding. Another important variable is the bone surface topography to which the cement will be made to come in contact with and adhere to. The more porous and the more irregular the bone surface is, the greater the bond strength will be between the bone and the cement.

In the situation of primary hip replacement, no previous joint replacement has been performed on that hip. This is the situation in which bone porosity and bone surface topography are the most favorable to allow for a strong cement-to-bone bonding. In the situation of primary joint replacement, the surfaces of the bone are that of live vascularised bone tissue. These bony tissues have a great deal of porosity. The porosity arises from Haversian canals, which are neurovascular micro-canals communicating with the bone's surface. In addition, there is generally cancellous bone attached to the cortical bone in the endosteal canal in a bone which has not been previously operated upon. This cancellous bone provides interstices into which cement can fill and interlock. This interlocking of cement into cancellous bone increases the bond strength of the cement to the host bone.

In the situation of revision hip replacement, the bone surface is different than it is for primary hip replacement. In the revision situation, the bone surface is not favorable for allowing a strong cement-to-bone bonding. This is because bone undergoes a biological and mechanical response to a previously cemented implant. As part of this response, the cortical endosteal bone surfaces become sclerotic. Also, all cancellous bone in the endosteal canal in the region of the previous implant has been lost. In revision hip replacement surgery, a failed implant is removed and a new implant is replaced. The endosteal canal of a removed failed femoral component is smooth and sclerotic. The bone surfaces in this situation have very low porosity and very low surface roughness. For these reasons, the ability of bone cement to bond securely to this type of endosteal surface is greatly compromised. Much orthopedic research has been devoted to observations of patients with total hip replacements. This research reveals that in revision cemented hip replacement surgery in humans, the time from implantation of the cemented femoral component until the cement-to-bone bond fails and loosening occurs is much shorter than for analogous primary surgery of the same type. The reasons for significantly poorer results in the revision situation are as follows: In revision surgery the poor mechanical and physical qualities of the bone limit the cement-to-bone bond strength. The low porosity of the bone, which is smooth and sclerotic in a revision situation, limits the ability of cement to bond to the bone. Also the loss of cancellous bone in the revision state decreases the cement's ability to bond to the bone. For these reasons the cement-to-bone bond strength is considerably weaker in revision than in primary femoral component replacement, in human total hip replacement surgery. The long term follow-up of thousands of human hip replacement patients confirms this.

Throughout the useful life of a joint replacement implant, that implant will be subjected to many stresses. The stresses will be frequent and repetitive. Factors known to affect the ability of a cemented hip replacement to withstand these stresses are as follows:

(a) The strength of the cement-to-bone bond. The weaker this bond is, the shorter the time period will be from implantation until failure of fixation. Failure of fixation of cement to the bone will result in mechanical and clinical failure of the implant.

(b) The strength of the cement-to-implant bond. This bond is generally stronger than the cement-to-bone bond. The cement-to-implant bond is not affected by the surgery being either primary or revision.

(c) Mechanical factors of the implant. These include modulus of elasticity. Also included is the ability of the implant to withstand cyclical loading. This is measured as the number of load cycles to mechanical failure of the implant.

(d) The thickness and uniformity of the cement mantle between the bone and the implant. This cement mantle secures the implant to the bone. The thicker and the more uniformly thick the cement mantle is, the better it will be able to withstand the stresses that are placed upon it. The better it is able to withstand those stresses, the longer the implant will remain in service.

(e) The mechanical factors of the bone. These include surface roughness and porosity. These factors affect the strength and longevity of the cement-to-bone bond.

The long term failure rate for a femoral prosthesis recemented at revision human hip replacement surgery is unacceptably high. For this reason, another method of fixing a prosthesis to bone has been developed. This other method is called biological fixation.

The most common method of fixing a femoral implant to bone without the use of cement is that of biological fixation. In this method, the femoral intramedullary canal is machined internally to the exact dimensions of the prosthesis to be implanted. A variety of implant sizes is available to facilitate this process. The prosthesis is coated at manufacture with a porous coating. The pore size is usually 200–400 microns in average size. Bone in contact with this type of implant surface will usually demonstrate some degree of bony ingrowth into the pores of the implant. This process usually takes six to twelve weeks from the time of implantation. When ingrowth occurs, it results in a strong mechanical interface between the bone and the implant. Using standard techniques, the long term success of human revision femoral component hip replacement surgery with biological fixation is significantly better than using cement for reimplantation. There are, however, a number of disadvantages of using a porous coated biological fixation type implant as opposed to a standard cemented one in human hip replacement surgery as follows:

(a) A high mismatch of modulus of elasticity between the implant and the bone will cause the patient to experience pain. The internal and external dimensions of the bone are a given. Since cement is not used in biological fixation hip replacement, a larger size femoral component must be used than had a cemented component been used. This is so because a cemented component would need to be smaller than the internal canal size of the femur, to allow room for the cement. Femoral components used are generally made from either of two materials; cobalt chromium alloy or titanium. Both of these materials have stiffness and moduli of elasticity considerably greater than that of bone. The thicker the implant is, the stiffer it will be. Thus, for a given size femur, there will be a higher mismatch of modulus of elasticity between bone and implant with a porous coated biological fixation implant than with a smaller cemented implant. This modulus of elasticity mismatch can produce symptoms of thigh pain when walking. There is a much higher incidence of thigh pain while walking in patients receiving porous coated biological fixation femoral implants then there is in patients receiving cemented femoral implants. This has been shown to be so in both human primary and revision hip replacement surgery, in multiple large studies done to date.

(b) Bone ingrowth into the porous coating does not always occur. For a porous coated implant to become attached to bone in a stable way, host bone must grow into the pores. The frequency of bone ingrowth in-vivo is not 100%. It is on the order of 98% in primary femoral component human hip replacement surgery. The frequency of bone ingrowth in revision femoral component surgery is on the order of 92%. Failure of bone ingrowth can lead to a painful mechanical failure of the implant.

(c) Weight bearing must be limited on the operative extremity. To minimize stress at the implant-bone interface and to maximize ingrowth potential, weight bearing is limited on the operative extremity for some time after surgery. This is temporary, but requires the patient to use ambulatory aids, such as crutches or a walker, for up to three months after surgery. With a cemented femoral stem, the patient could fully bear weight on that femur immediately.

(d) A biological fixation type implant can migrate before ingrowth occurs. The bond of the porous coated implant to the bone depends upon the ingrowth of bone into the porous coating for strength and stability. Thus, the implant will not achieve optimal implant stability for six to twelve weeks after implantation. During this time period, if stresses on the implant exceed its preliminary press fit mechanical strength at its interface, the implant will move relative to the host bone. In the femur, the implant may change position vertically or rotationally. The implant may subside into the femoral canal. Subsidence will result in shortening of the operative limb and a limb length discrepancy may result. Such a shortening of the limb length at the hip will affect the soft tissue balance at the hip joint. The soft tissue balance provides the necessary mechanical forces to prevent hip dislocation. Thus a subsidence of the femoral stem may result in hip joint instability. This may predispose the patient to hip joint dislocations after surgery. In addition to vertical migration, it is possible for the prosthesis to make a rotational migration relative to the host bone. A rotatory migration of the femoral component will also affect stability of the hip. In addition, rotatory migration of the femoral component will affect the range of motion of the joint. In contrast, a cemented femoral component is stable immediately, and can not migrate relative to the femur.

(e) The cost of manufacture is considerably higher to produce a porous coated component compared to a standard component. This is because an expensive extra step is required to apply the porous coating to the prosthesis. Femoral components that are implanted with cement are generally not porous coated.

To the inventor's knowledge, no one has previously disclosed a method or apparatus for placing grooves in a bone for the purpose of improving cement-to-bone bonding. U.S. Pat. No. 4,550,788 to Park (1985) discloses a roof bolt hole groover. This is a drilling device for use in bolting together a discontinuous rock mass in order to provide a safe mine roof. The grooving portion of this device includes at least two groove bits that reciprocate pivotally for the purpose of scoring the surface of the hole being drilled. This is primarily a drilling device, and secondarily a scoring device. This device has a grooving mechanism coupled to a drilling mechanism. The two mechanisms are coupled by a series of gears so that the two operations are done simultaneously. The purpose of this device is to score a hole while it is being drilled. This device would be impractical to use to create multiple grooves inside the diaphysis of a bone. This device is not easily disassembled for cleaning purposes, as would be required of a medical device suitable for grooving of bone. The reciprocating mechanism for the grooving bits is a significant disadvantage to its application as a groover. The bits reciprocate toward and away from the main axis of the device while it is in operation. This will result in a tendency for the device to move axially at the point of operation in which the groove bits are maximally retracted. This, in turn, would result in inaccuracies in grooving, and groove widening. Thus this device is not conducive to making finely controlled grooves in human bone during surgery, where accuracy is of great importance. This device is not intended to create circumferential grooves while remaining stationary in an axial direction. It will not work well to cut multiple grooves of constant width, depth, or spacing. The non-reproducibility of exact grooving patterns would significantly limit its usefulness in the medical field for cutting grooves in live human bone. This device contains an end cutting drill. This drill could damage the bone or material being machined in unintended ways if attempting to use the grooving mechanism to cut thin uninterupted grooves. This device has no intended medical uses.

U.S. Pat. No. 3,472,229 to Kuntscher (1969) discloses an instrument for cutting or severing a bone from the inside thereof. This device consists of a surgical saw having an elongated flexible shank and drive support. This device is intended for severing a bone from the inside. This device could be used to cut grooves in a bone. However, to do so would be quite difficult. There would be minimal if any visibility at the cutting site. The operation of this device would most likely require x-ray flouroscopic monitoring. The resultant radiation exposure would have risks to the patient and nearby personnel. The cutting saw is such that it is generally at an acute angle to the bone. This acute angle would make circumferential grooving of the bone's endosteal canal very time consuming and difficult. The saw will have a great tendency to bounce off of the bony surface while cutting. This is because of the long lever arm controlling the saw. This device will work poorly to cut multiple circumferential grooves of constant width, depth, or spacing. The non-reproducibility of exact grooving patterns is a significant disadvantage of this device when used for grooving a bone canal.

U.S. Pat. No. 3,435,729 to Toth (1967) discloses a hole grooving device. The purpose of this device is for toughening the inner formed finger holes of a bowling ball. This device contains a pair of semi-cylindrical body members containing the grooving mechanism, and an elongated rod extending radially from the body members which is the mechanism of deployment of the cutting member of this device. This device has several disadvantages which make this a poor if not useless tool for grooving the intramedullary canal of a long bone. One major disadvantage of this device is that the deployment mechanism results in the two semi-cylindrical body members moving apart from each other and pushing against the walls of the hole being machined. This creates excess friction between the device and the hole being machined. This will also tend to deform the hole being machined. In a bone, this could easily result in a fracture of the bone if too much pressure is applied against the inner walls of the bone canal by the body of this device. Another disadvantage of this device is that the elongated rod extending radially from the body of this device will impinge upon bone and soft tissues if used to groove the canal of a long bone during live surgery. In the human femur during hip replacement surgery, this rod would impinge upon the greater trochanter, making the device useless for producing circumferential grooves in the intramedullary canal of the proximal femur.

U.S. Pat. No. 5,387,218 to Meswania (1995) discloses a surgical instrument for shaping bone. This device functions as a motorized broach to machine the intramedullary canal of a bone. This device however, does not have a retractable cutting member. It therefore can not produce grooves in the diaphyseal portion of an intramedullary bone canal. This device is designed to machine and shape the bone, and not to machine circumferential grooves into the bone's surface. Since the cutting surface is only on one side of this device, and since the entire device can only move axially in the bone, this device can not be used to produce circumferential grooves in any portion of the bone canal.

SUMMARY OF OBJECTS AND ADVANTAGES OF THE INVENTION (a) To provide a method and a novel apparatus to machine grooves into the intramedullary canal of a bone so that the bone's internal shape will allow for an improved cement-to-bone bonding in prosthetic joint replacement.

(b) To provide a groover that will not impinge upon surrounding structures while machining grooves in the intramedullary canal of a long bone during live surgery. A major novel advantage of this invention over prior art is that the external mechanism for deployment of the cutters is located proximal to the driving device. The internal mechanism for deployment of the cutters is housed within the driving shank of the invention. The invention is designed to be operated by a motorized device which drives the invention via a cannulated chuck. The cannulated chuck transmits the mechanism for deploying the cutters internally through and out the proximal end of the driving device. This significant advantage over prior art is critically important in live orthopedic surgery. This advantage prevents the external mechanism for operating the cutters from damaging vital structures during live surgery. During hip replacement surgery, these vital structures include the sciatic nerve, greater trochanter of the femur, and surrounding musculature and blood vessels. The inventor believes that there is no previously described device suitable for grooving the intramedullary canal of the human femur during live hip replacement surgery containing all of the advantages of the present invention. The inventor also believes that the disadvantages cited relating to prior art precludes prior art groovers from being applicable to use as an intramedullary bone groover for safe use in live orthopedic hip replacement surgery.

(c) To use opposing cutters, which is a significant advantage of the invention over prior art. In prior art groovers that contain only one cutter, when the cutter pushes against the walls of the hole being machined, an equal and opposite force will push the groover back towards and against the opposing wall, resulting in significant friction between the housing and the walls of the hole. In groovers of the invention, opposing cutters contact the walls of the hole with equal force, and no significant force between the housing and the hole is generated. Thus there is substantially less friction between the housing and the walls of the hole than when using prior art cutters, employing a single cutter.

(d) To provide a groover similar in general shape to the basic reamer used in human hip replacement surgery to prepare the intramedullary canal of a long bone without excess friction or pressure upon the wall of the bone canal, whereby the grooving step will be easily and conveniently incorporated into present surgical practice.

(e) To provide a groover that will machine the intramedullary canal of a long bone without excess friction or pressure upon the walls of the bone canal.

(f) To allow implantation of a cemented femoral component in revision hip replacement surgery with improved cement-to-bone bonding over techniques previously in use.

(g) To allow implantation of a cemented femoral component in primary hip replacement surgery with improved cement-to-bone bonding over techniques previously in use.

(h) To allow improved cement-to-bone bonding in any situation where a prosthetic implant is cemented to a bone This would pertain to any such situation in which the bone can be grooved with this invention. This includes human, veterinary, and dental uses.

(i) To allow improved bonding of cement-to-bone when allograft bone is used in hip replacement surgery. This would include cementing a prosthesis into the grooved intramedullary canal of an allograft femur or portion thereof.

(j) To allow improved bonding of cement to any bone where this invention is used to create grooves in that bone. This would include bone that is part of a living being, and also bone that is not part of a living being.

(k) To allow any suitable object or biological material to be grooved or machined by this invention.

(l) To machine grooves accurately into any suitable material with a reproducible pattern of grooves of constant width, depth, and spacing.

(m) To machine finely controlled circumferential grooves in bone safely during surgery.

(n) To provide a groover suitable for use during human bone and joint surgery that is easily disassembled and reassembled by its user for cleaning, sterilization, and part replacement.

These and other objects and advantages will become apparent from a consideration of the ensuing description and drawings.

BRIEF DESCRIPTION OF THE DRAWINGS

In the drawings, closely related figures have the same number but different alphabetic suffixes.

DESCRIPTION OF THE PREFERRED EMBODIMENTS

Figure 1:
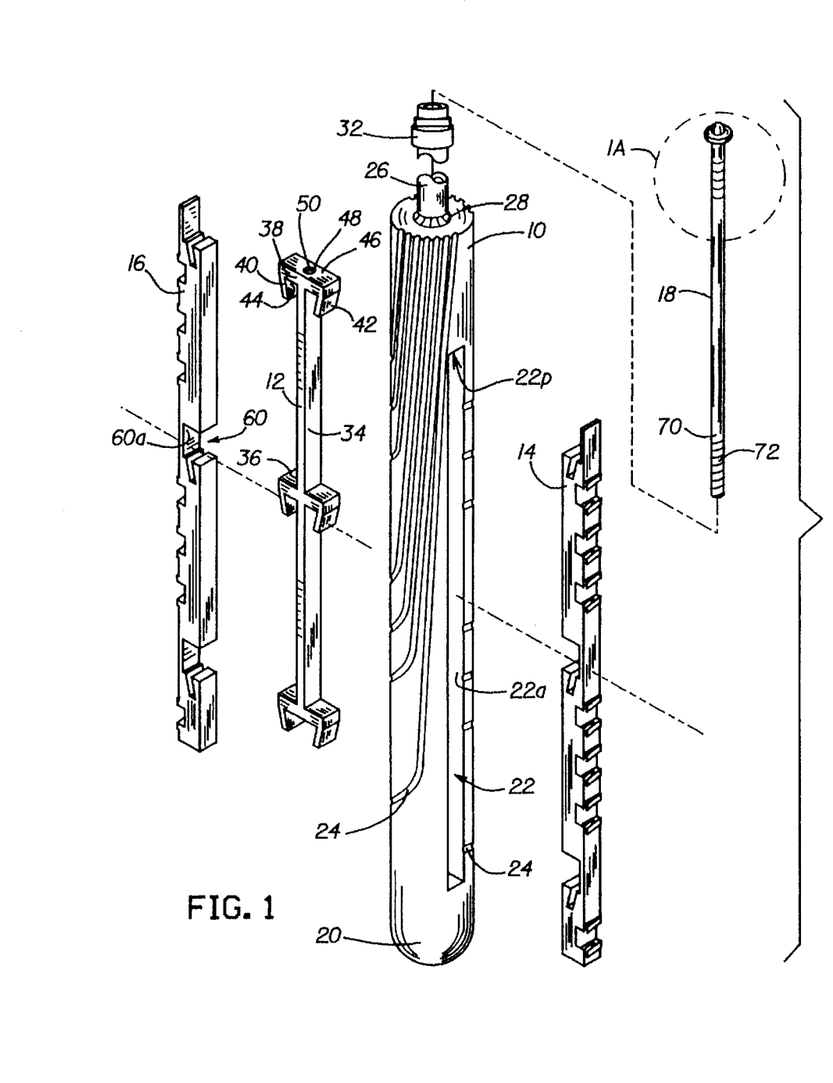
FIG. 1 is an exploded perspective view of a preferred embodiment of the invention.

Referring to the drawings, FIG. 1 a housing 10, an actuator 12, two cutting members 14 and 16, and an actuator rod 18.

Housing 10 is formed from rigid material. Housing 10 has a cylindrical shape in its long axis. Housing 10 is uniform in diameter except at its distal portion 20. Distal portion 20 of housing 10 is hemispherical in shape. Housing 10 is preferably formed with a rectangular cutout 22 through the main body of housing 10. Cutout 22 is uniform in its dimensions of height and width throughout housing 10. The dimensions of height and depth of each of the two inner rectangular sagital faces 22a of cutout 22 are identical for corresponding dimensions in each of two faces 22a. The portions of cutout 22 in contact with the outer surface of housing 10 are identical in the dimensions of height and width on either side of the housing. The inner surface of cutout 22 is formed smooth. Optional grooves 24 may be formed in housing 10. Grooves 24 are recessed into the surface of housing 10. Grooves 24 begin at cutout 22 of housing 10 at regular intervals in perpendicular orientation to one side of the height of cutout 22. Grooves 24 then proceed in a proximal direction. Adjacent grooves 24 do not communicate with each other. Grooves 24 are formed such that all grooves beginning proximally on one side of height of cutout 22 will remain in their entirety on the same side of housing 10 as shown in FIG. 1. The portion of housing 10 that is proximal to the proximal most portion of cutout 22 is cannulated in an axial direction centrally in the body of housing 10. The diameter of this cannulation is slightly larger than the diameter of the main body of actuator rod 18. A drive shaft 26 is formed from rigid material. Drive shaft 26 is attached to the proximal portion of housing 10. Drive shaft 26 is preferably welded or machined to the proximal end of housing 10 such that there is a radius 28 of rigid material at the outer surface of the juncture of housing 10 and drive shaft 26. Drive shaft 26 is cannulated axially such that this cannulation is centered within the axial plane of drive shaft 26. The axial cannulation of drive shaft 26 is perfectly in line with the cannulation in the proximal end of housing 10. The cannulation of drive shaft 26 is identical in diameter to the cannulation in proximal portion of housing 10. The cannulation of drive shaft 26 communicates with cannulation in proximal portion of housing 10. A mechanism for attachment to a motorized driving device 30 is preferrably formed into proximal end of drive shaft 26. As shown in FIG. 1 a male end 32 of a quick release type chuck 84 is the mechanism for attachment of drive shaft 26 to motorized driving device 30 in the preferred embodiment.

Actuator 12 is formed from rigid material. The main body of actuator 12 comprises a long rectangular shaped beam containing opposing broad surfaces 34 as well as anterior surfaces and posterior surfaces. A plurality of pressure arms 36 are formed at regular intervals along the broad surfaces 34 of main body of actuator 12. All pressure arms 36 have similar shapes and dimensions to each other. At each pressure arm 36 level of actuator 12, two isometrically shaped pressure arms 36 are located directly across opposite broad surfaces 34 of actuator 12. Each pressure arm 36 comprises a proximal portion 38 and a distal portion 40. All pressure arms 36 are similar in all dimensions thereof. Proximal portion 38 of pressure arm 36 extends out from and perpendicular to broad surface 34 of actuator 12. All proximal portions 38 of all pressure arms 36 each contain a proximal facet and a distal facet. Distal portion 40 begins proximally at the lateral most area of proximal portion 38 and then extends distally and diagonally inward toward broad surface 34 of actuator 12. There is a gap between the distal most end of distal portion 40 and broad surface 34 of actuator 12. All distal portions 40 of all pressure arms 36 each contain an outer facet 42 and an inner facet 44. The anterior to posterior dimensions of main body of actuator 12 are identical to the anterior to posterior dimensions of both proximal portion 38 and distal portion 40 of pressure arm 36. All faces of pressure arm 36 are flat. The height of pressure arm 36 is defined as the dimension of the shortest distance measured along axis of broad surface 34 of actuator 12 between proximal facet of proximal portion 38 and a line drawn perpendicular to and outward from broad surface 34 which intersects the distal most end of distal portion 40. The height of distal portion 40 of pressure arm 36 is defined as the dimension of the shortest distance measured along broad surface 34 of actuator 12 between the distal facet of proximal portion 38 and a line drawn perpendicular to and outward from broad surface 34 which intersects the distal most end of distal portion 40. A proximal surface 46 of actuator 12 is flat and rectangular in shape. A recessed threaded hole 48 is formed centrally in proximal surface 46 of actuator 12. Recessed hole 48 contains female threads 50 in its walls.

Figures 1A, 2, 2A:
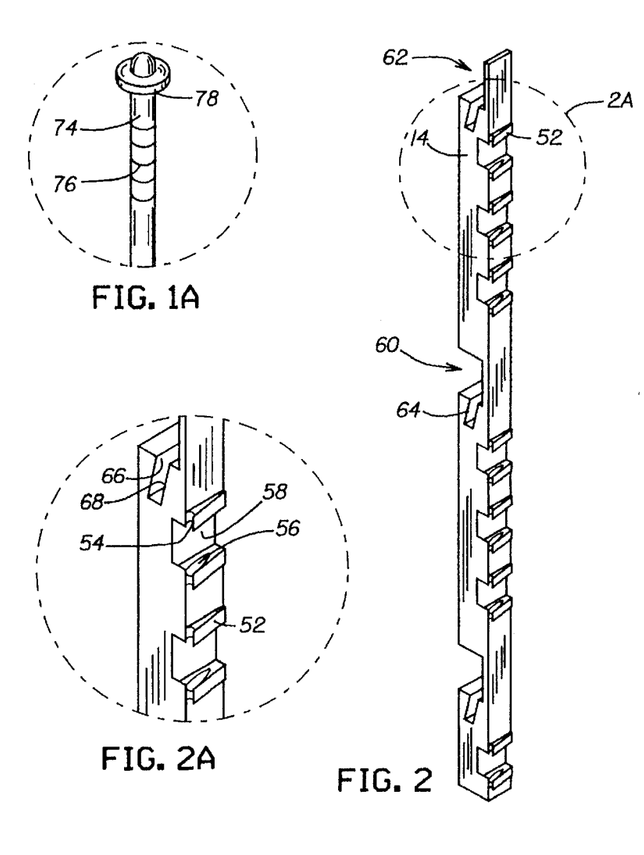
FIG. 1A is an enlarged portion of FIG. 1, showing the top of the proximal actuator rod.
FIG. 2 is a perspective view of one of the cutting members shown in FIG. 1.
FIG. 2A is an enlarged perspective view of a portion of a cutting member.

Cutting members 14 and 16 are formed from rigid material. FIG. 2 depicts cutting member 14. Cutting member 16 is identical to cutting member 14. Cutting member 14 comprises a beam shaped element with several faces. The outer face of cutting member 14 contains a plurality of cutting teeth 52 in the preferred embodiment. An enlarged view of a portion of cutting member 14 is demonstrated within the encircled view 2A. Referring to FIG. 2A, cutting teeth 52 are shaped with a cutting surface 54 on one side of each tooth 52. All cutting surfaces 54 are oriented in the same direction. Tooth grooves 56 are formed on the proximal surface of every other cutting tooth 52. Recessed notches 58 are relieved on outer face of cutting member 14 between adjacent cutting teeth 52. Recessed notches 58 are located at every third cutting tooth 52. Tooth grooves 56 and recessed notches 58 are positioned relative to each other such that the cutting tooth 52 located at the distal portion of recessed notch 58 will have a tooth groove 56 on its proximal surface. In the preferred embodiment as demonstrated in FIG. 2, the inner face of cutting member 14 contains at least one recessed mortise 60. With the exception of a proximal most mortise 62, each mortise 60 contains three faces; a flat proximal mortise face, a flat inner mortise face 60a, and a distal mortise face. Proximal most mortise 62 is formed without a proximal mortise face. An angled notch 64 is relieved in distal mortise face. Angled notch 64 is directed distally and toward the inner face of cutting member 14. Angled notch 64 contains three surfaces; an inner notch surface 66, an outer notch surface 68, and a distal notch surface. The height of inner mortise face 60a is defined as the shortest distance between between proximal mortise face and distal mortise face of same mortise 60. The depth of angled notch 64 is defined as the dimension of the shortest distance measured along inner notch surface 66 between distal mortise face and distal notch surface. Except for proximal most mortise 62, the height of inner mortise face 60a is slightly greater in dimension than the height of pressure arm 36. The length of distal portion 40 of pressure arm 36 will be of similar dimension to the depth of angled notch 64. The overall length of cutting member 14 will be slightly less in dimension than the height of cutout 22. The anterior face and the posterior face of cutting member 14 are both flat.

Actuator rod 18 is shown in FIGS. 1 and 1A. Actuator rod 18 is formed from rigid material. Actuator rod 18 comprises a cylindrical rod. A distal end 70 of actuator rod 18 is threaded with male threads 72. As demonstrated in FIG. 1A, a proximal end 74 of actuator rod 18 contains gradations 76. Proximal to gradations 76 is a button collar 78. The diameter of the main body of actuator rod 18 is slightly smaller in dimension than the diameter of cannulation of drive shaft 26.

Figures 3, 3A:
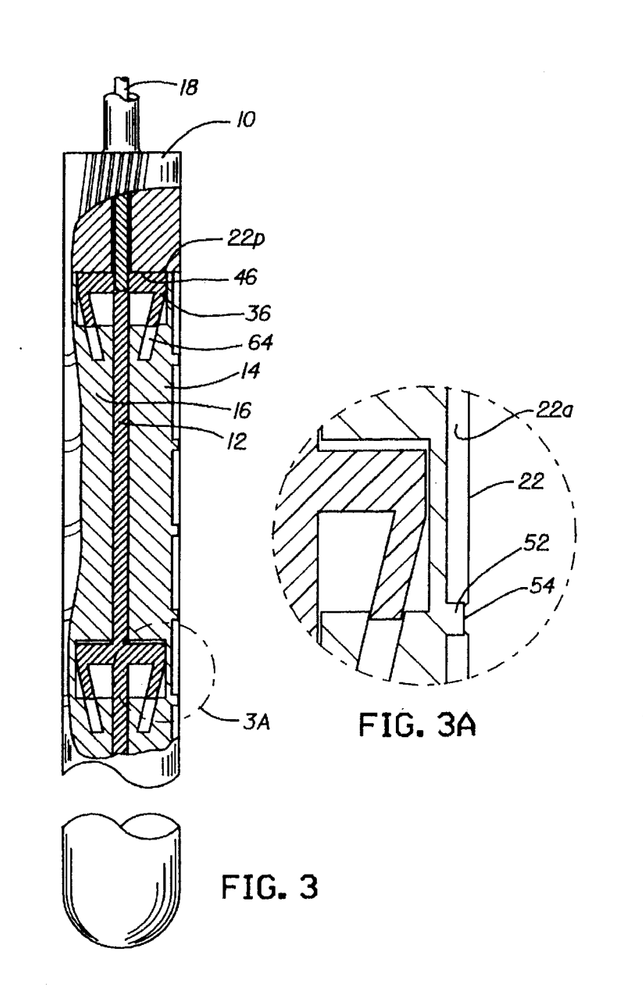
FIG. 3 is a partially sectioned side view of the same embodiment, showing the cutting members fully retracted inward.
FIG. 3A is an enlarged a portion of FIG. 3, showing the mechanism for moving a cutting member.
Figure 4:
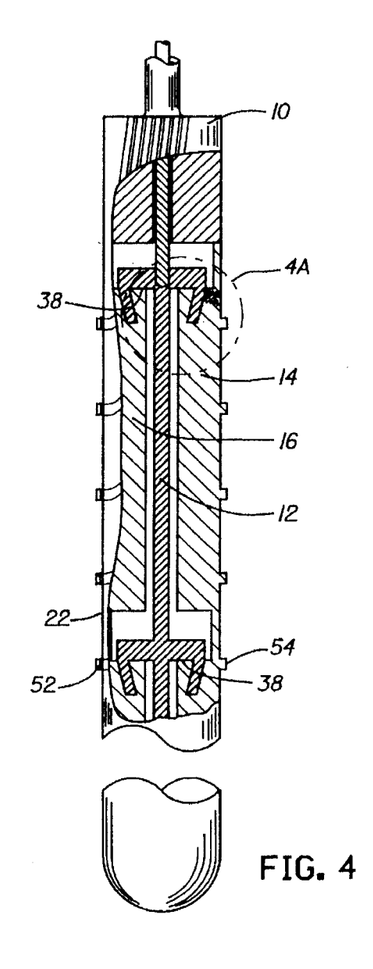
FIG. 4 is a view corresponding to FIG. 3, but showing showing the cutting members fully deployed outward.

FIGS. 3 and 4 show housing 10, actuator 12, cutting members 14 and 16, and actuator rod 18 assembled in the preferred embodiment. It is very important that in the retracted state as seen in FIG. 3, that the distance between proximal transverse inner face 22p of cutout 22 and proximal surface 46 of actuator 12 is slightly less in dimension than the height of pressure arm 36. This is important to prevent pressure arms 36 from being able to disengage their corresponding angled notches 64 while the unit is assembled.

FIG. 3 shows the assembled invention with cutting elements 14 and 16 maximally retracted into housing 10. In this retracted state, actuator 12 is retracted maximally proximally with proximal surface 46 impinging upon proximal transverse inner face 22p. In this retracted state, as seen in the encircled enlarged view FIG. 3A all cutting surfaces 54 of all cutting teeth 52 are withdrawn completely inside cutout 22.

FIG. 4 shows the assembled invention with cutting members 14 and 16 maximally deployed outward from housing 10. In this deployed state actuator 12 is displaced maximally distally with distal facet of proximal portion 38 impinging upon distal mortise face. In this deployed state, all cutting surfaces 54 of all cutting teeth 52 are deployed outside of cutout

DESCRIPTION OF ADDITIONAL EMBODIMENTS

Figure 4A:
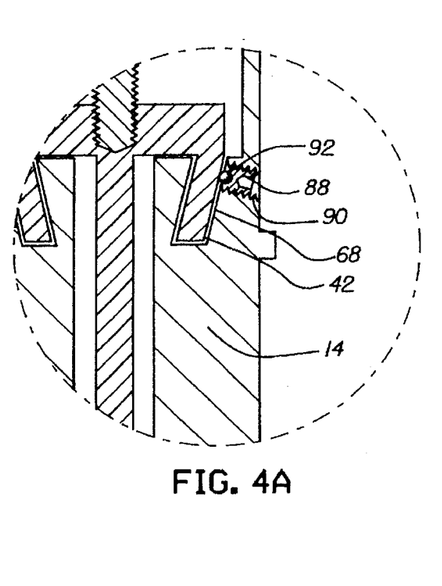
FIG. 4A is an enlarged view of a portion of FIG. 4, showing detail of an optional embodiment of the invention.

FIG. 4A shows an optional embodiment of the invention. In this embodiment, a ball plunger 88 is placed into a corresponding threaded hole 90 in cutting member 14. Threaded hole 90 extends between outer face of cutting member 14 and outer notch surface 68. A ball bearing 92 of ball plunger 88 is in contact with outer facet 42 of distal portion 40 of pressure arm 36. In this optional embodiment, ball bearing 92 will function as a mechanism for reducing friction between outer facet 42 of pressure arm 36 and outer notch surface 68 of cutting member 14.

Figures 5, 5A:
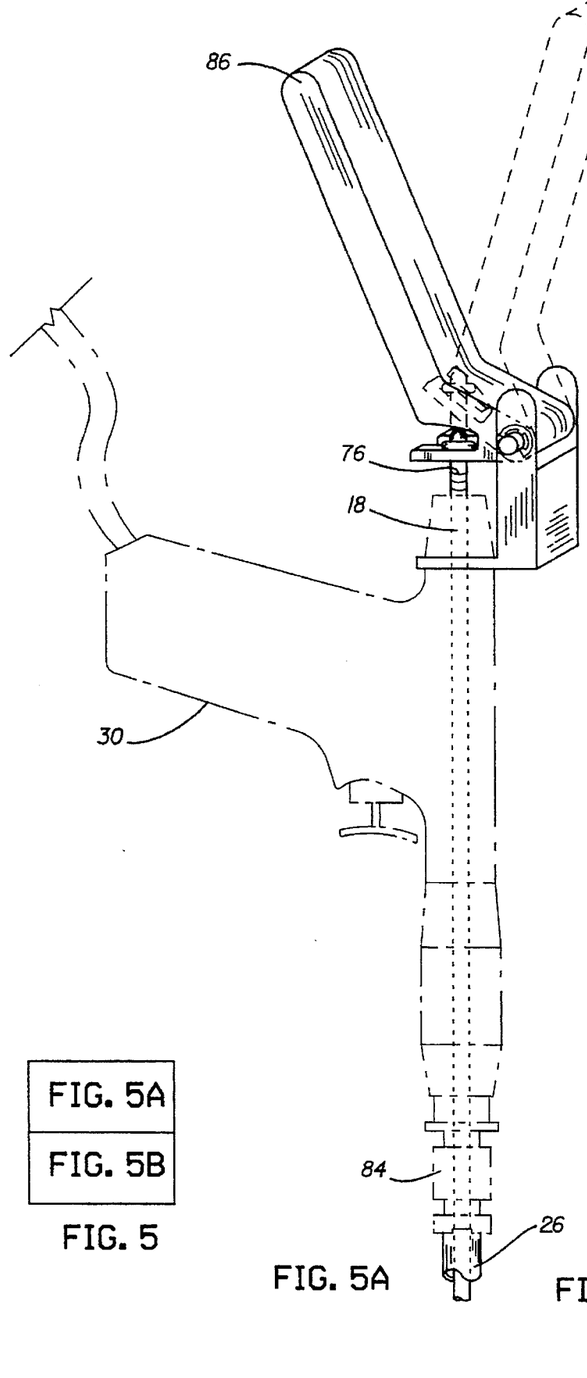
FIG. 5 is a schematic combination of FIGS. 5a and 5b, which show a perspective view of a preferred embodiment of the invention as assembled with a motorized driving device.
FIG. 5A is a perspective view of said motorized driving device and containing a lever device for operation of said actuator rod.
Figure 5B:
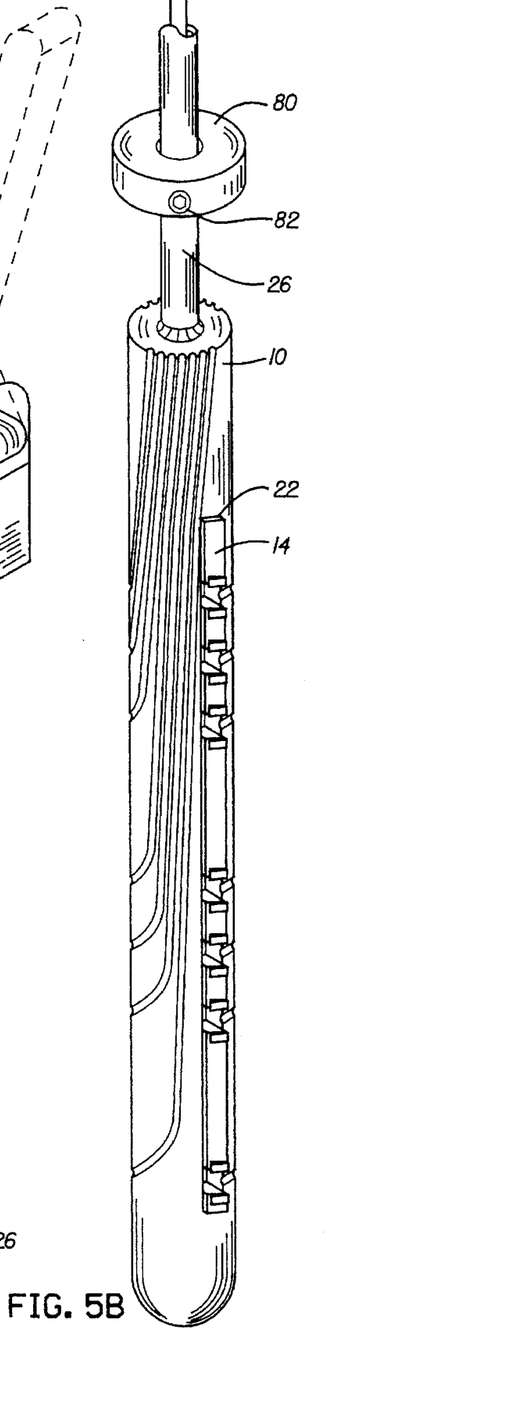
FIG. 5B is a perspective view of said embodiment of the invention but adding a collar on drive shaft.

FIG. 5 shows additional embodiments of the invention. In this figure a collar 80 is shown on drive shaft 26. Collar 80 is stabilized relative to drive shaft 26 by a set screw 82. The purpose of collar 80 is to prevent further distal axial movement of housing 10 relative to the material being machined once collar 80 comes in contact with that material. It is not important whether collar 80 is placed on drive shaft 26, or whether a similar collar with a larger hole is placed on housing 10. It is very important however that if collar 80 is used on housing 10 that collar 80 is secured to housing 10 proximal to the proximal most portion of cutout 22, so as not to interfere with the deployment of cutting members 14 and 16. FIG. 5 also shows the invention attached to cannulated motorized driving device 30 by a cannulated quick release chuck 84, via quick release male end 32 of drive shaft 26. Also demonstrated in this figure is a lever device 86 to control the movement of actuator rod 18. Lever device 86 is placed at and is attached to the proximal end of cannulated motorized driving device 30. Visible gradations 76 on actuator rod 18 allow the user to determine to what extent cutting members 14 and 16 are deployed or retracted.

Figure 6:
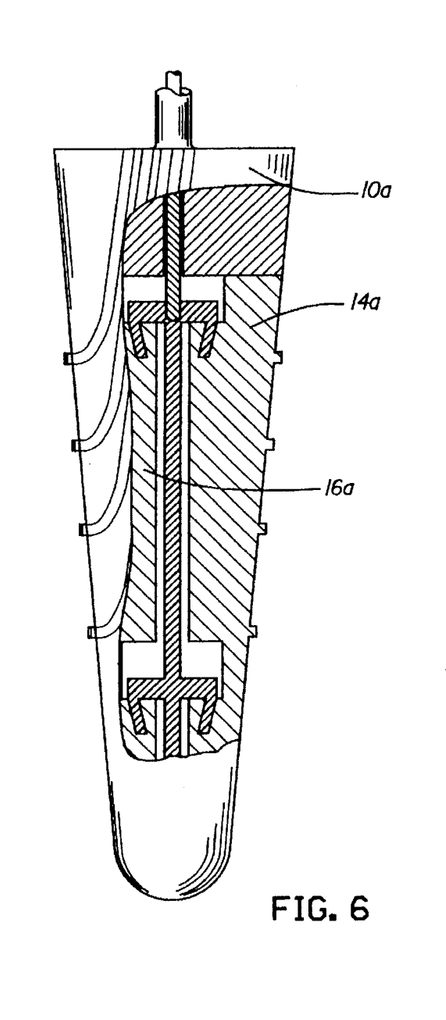
FIG. 6 is a partially sectioned side view of a conical shaped embodiment of the invention.

FIG. 6 shows another optional embodiment of the invention. Housing 10a in this embodiment is conical in shape. Cutting members 14a and 16a have generally trapezoidal dimensions such that outer faces of cutting members 14a and 16a are parallel to the outer surface of housing 10a. This embodiment may be used to form grooves in a conical shaped hole of similar dimensions to that of housing 10a. The description of the basic preferred embodiment will apply to this optional embodiment.

Figure 7:
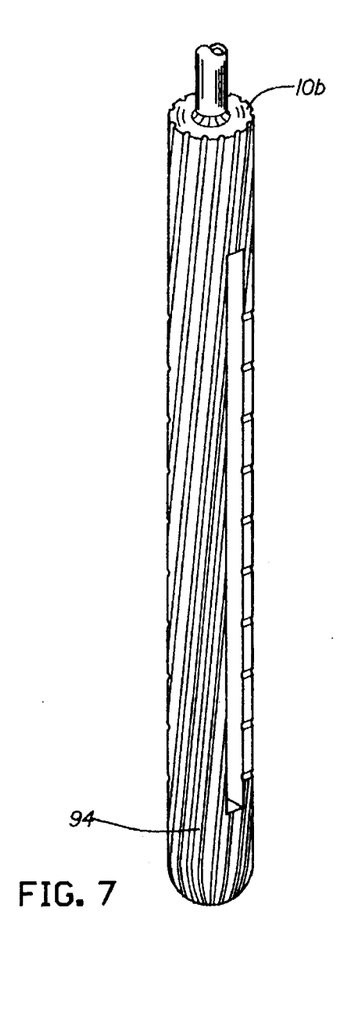
FIG. 7 is a perspective view of an optional embodiment of the housing of the device containing twist reamer teeth on the surface of the housing.

FIG. 7 shows an optional embodiment of housing 10b. This optional embodiment is different from the basic preferred embodiment in the external topography of housing 10b. In this embodiment, housing 10b contains twist reamer teeth 94 around the external surface of housing 10b.

Figure 8:
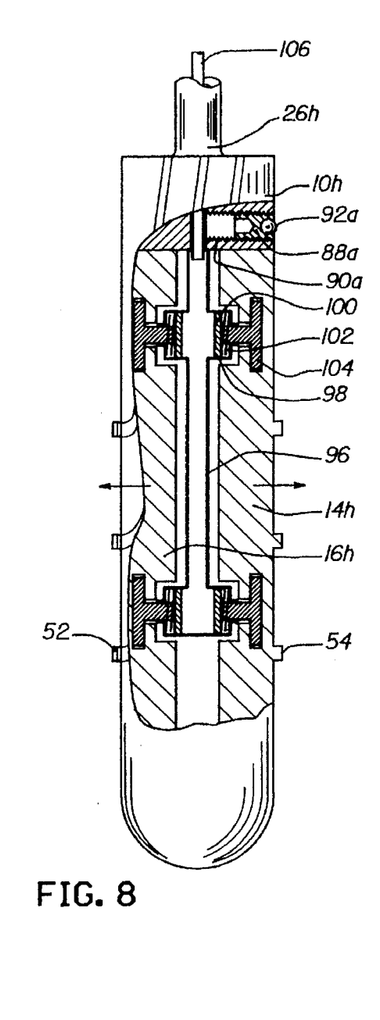
FIG. 8 is a partially sectioned side view of an optional embodiment of the invention whereby the mechanism for moving the cutting members is hydraulically operated.

FIG. 8 shows yet another optional embodiment of the invention. In this embodiment, the mechanism for moving cutting members 14h and 16h is hydraulically operated by a sealed hydraulic system. In this embodiment, the hydraulic actuator mechanism consists of an actuator tube 96 containing a plurality of slave cylinders 98. Each slave cylinder 98 contains a piston 100 and a return spring 102. A plunger 104 connects each piston 100 to cutting member 14h or 16h. A pipe 106 is shown inside cannulation of drive shaft 26h and inside cannulation of proximal housing 10h. Pipe 106 is used to convey hydraulic fluid and to transmit hydraulic pressure into actuator tube 96 from a remote location.

Also shown in FIG. 8 is a ball plunger 88a inserted into a corresponding threaded hole 90a in proximal portion of housing 10h. In this optional embodiment, a ball bearing 92a will function as a mechanism for reducing friction between outer surface of housing 10h and walls of the material being machined.

OPERATION

The device is assembled prior to its use. Firstly, all pressure arms 36 of actuator 12 are made to engage corresponding angled notches 64 of cutting members 14 and 16. Pressure arms 36 are deployed fully into angled notches 64 and this partial assembly is then inserted into cutout 22 of housing 10. Collar 80 is attached to drive shaft 26 or proximal housing 10. Next, male end 32 of drive shaft 26 is connected to driving device 30 via chuck 84. Actuator rod 18 is inserted from proximal to distal through driving device 30, drive shaft 26 cannulation, and proximal housing 10 cannulation until it engages threaded hole 48 of actuator 12. Actuator rod 18 is then turned to screw male threaded 72 end of actuator rod 18 into female threaded 50 hole 48 of actuator 12 until tight and fully seated. Lever device 86 is inserted onto driving device 30 and lever device 86 engages button collar 78 of actuator rod 18. After completing the above assembly steps, the invention is assembled and is operational. By reversing the above assembly steps, the device can be completely disassembled for cleaning or part replacement.

Housing 10 portion of the assembled device is then inserted into a previously prepared cylindrical hole of similar dimensions. In the intramedulllary canal of a long bone, this will usually be accomplished by first preparing the canal with a cylindrical reamer of similar diameter to the diameter of housing 10. With the housing inserted into the previously prepared hole to the desired depth, collar 80 is adjusted distally until collar 80 contacts the material being machined. Set screw of collar 80 is tightened. Next, driving device 30 is activated, resulting in rotation of the invention within the previously prepared hole. While the invention is rotating, lever device 86 is used to deploy actuator rod 18 distally into drive shaft 26. This in turn will force actuator 12 distally within housing 10. This will then force pressure arms 36 distally into corresponding angled notches 64. As this occurs, outer facets 42 of pressure arms 36 will push radially outward against outer notch surfaces 68 of cutting members 14 and 16. This will deploy cutting members 14 and 16 radially outward from housing 10. As cutting members 14 and 16 move outward, cutting surfaces 54 will be forced into contact with the walls of previously prepared hole. As the invention rotates, cutting surfaces 54 will then proceed to cut circumferential grooves within the walls of the previously prepared hole. By carefully controlling lever device 86 and observing gradations 76 during the grooving operation, the depth of the grooves cut can be carefully controlled. Tooth grooves 56, recessed notches 58, and grooves 24 channel debris away from cutting surfaces 54 during the grooving operation.

After grooving is completed, lever device 86 is used to withdraw actuator rod 18 proximally. This will then force pressure arms 36 proximally within angled notches 64. As this occurs, inner facets 44 will push radially inward against inner notch surfaces 66 of cutting members 14 and 16. This will displace cutting members 14 and 16 inward into cutout 22. When cutting members 14 and 16 are maximally retracted into housing 10, the device is removed from the previously prepared hole.

FIG. 8 shows an optional embodiment of the invention whereby the mechanism for moving cutting members 14h and 16h is hydraulically operated by a sealed hydraulic system. The method of operation of this optional embodiment is as follows: The assembly of invention is attached at proximal end of drive shaft 26h to motorized driving device 30 via cannulated chuck 84. The assembly of invention is then inserted into a previously prepared cylindrical hole of similar dimensions. After housing 10h is inserted into the previously prepared hole, driving device 30 is activated. This will result in rotation of the invention within the previously prepared hole. While the assembly of invention is rotating, a remote hydraulic pressure source is used to place fluid in pipe 106 under positive hydraulic pressure. As this is a sealed hydraulic system, this will result in hydraulic positive pressure being applied to pistons 100. This will force pistons 100 outward, which will in turn force plungers 104 outward. This will deploy cutting members 14h and 16h radially outward from housing 10h. As cutting members 14h and 16h move outward, Cutting surfaces 54 of cutting teeth 52 will be forced into contact with the walls of the previously prepared hole. As the assembly of invention rotates, cutting surfaces 54 will then proceed to cut circumferential grooves within the walls of the previously prepared hole. After grooving is completed, hydraulic pressure from remote hydraulic pressure source is released. Return springs 102 will then force pistons 100 and attached plungers 104 inward. This in turn will displace cutting members 14h and 16h back inward into housing 10h. When cutting members 14h and 16h are maximally retracted into housing 10h, the assembly of invention is withdrawn from the previously prepared hole.

I claim:

1. A tool for grooving the inside wall of a hole in intramedullary bone, comprising a housing having a central axis and elongated along its central axis and having a circular cross-sectional shape when viewing a section through a plane perpendicular to said central axis, a cannulated shank at one end of the housing, the shank being connectable to and rotatable by rotary power means, a pair of cutter means each comprising at least one cutting edge, means mounting said cutter means in the housing for opposite movement radially of said axis to project said cutting edges beyond the housing sufficiently for grooving said inside wall, and to retract said cutting edges sufficiently to permit insertion of the tool into said hole and withdrawing it therefrom, an elongated control means extending through the cannulation of the shank, and means coupling the control means to the cutter means to cause the cutter means to move radially outwardly when the control means moves lengthwise of the tool in one direction and to move radially inwardly when the control means moves lengthwise of the tool in a direction opposite to said one direction.

2. A tool according to claim 1, in which the cannulated shank is connectable to and rotatable by a rotary power unit of the kind which is holdable and directed by hand, and the cannulated shank is cannulated along its axis of rotation.

3. A tool according to claim 2 in which its said elongated control means is of sufficient length to pass through and beyond a rotary power unit of said kind, thereby exposing an end of said elongated control means for activation to control said cutter means.

4. A tool according to claim 1 in combination with a rotary power unit having a distal end and a proximal end, said proximal end being connected to said shank and thereby rotate the tool, said power unit being cannulated along its axis of rotation, and said elongated control means of the tool being extended through said shank and through said power unit to project from said distal end of the power unit, and in combination with a control member mounted on the power unit and connected to a part of the elongated control means projecting from said distal end of the power unit, said control member being operable during rotation of the power unit and tool to move the elongated control means lengthwise to move said cutter means of the tool to and from a cutting position.

5. The combination of claim 4, in which said tool, said power unit and said control member are holdable and directable by hand for guiding and operating the tool during its grooving of a bone.

6. A tool according to claim 1, in which said housing is generally cylindrical in exterior shape.

7. A tool according to claim 1, in which said housing is generally conical in exterior shape.

8. A tool according to claim 1, in which an opening extends transversely through the housing and across said central axis, each cutter means being mounted in said opening and being moveable outwardly and inwardly of said housing in a direction substantially perpendicular to said central axis.

* * * * *